United States Patent

Weigold

[11] Patent Number: 6,055,848
[45] Date of Patent: May 2, 2000

[54] AIR QUALITY MEASURING DEVICE

[75] Inventor: Thomas Weigold, Sinzheim, Germany

[73] Assignee: Robert Bosch GmbH, Stuttgart, Germany

[21] Appl. No.: 09/269,099

[22] PCT Filed: Jul. 26, 1997

[86] PCT No.: PCT/DE97/01577

§ 371 Date: Jun. 9, 1999

§ 102(e) Date: Jun. 9, 1999

[87] PCT Pub. No.: WO98/12547

PCT Pub. Date: Mar. 26, 1998

[30] Foreign Application Priority Data

Sep. 19, 1996 [DE] Germany ............... 196 38 204

[51] Int. Cl.[7] ............... G01N 27/12; G01N 1/00; G01N 37/00
[52] U.S. Cl. ............... 73/31.05; 73/23.2; 73/23.34; 73/31.01; 73/335.05; 324/691; 324/712; 340/634; 422/98; 422/90; 236/44; 236/49.2; 165/249; 237/12.6
[58] Field of Search ............... 73/31.05, 31.01, 73/31.03, 23.2, 23.34, 29.05, 335.02, 335.05; 324/71.1, 549, 691, 705, 711, 712; 340/634, 633, 632; 422/83, 90, 98, 97; 236/44 E, 44 C, 49.2, 49.3, 91 C, 91 G, 94, DIG. 19; 237/5, 12.5, 12.6, 229; 165/223, 291, 249

[56] References Cited

U.S. PATENT DOCUMENTS

| | | | |
|---|---|---|---|
| 4,166,380 | 9/1979 | Batz . | |
| 4,306,444 | 12/1981 | Hattori et al. | 73/23 |
| 4,327,361 | 4/1982 | Berlin . | |
| 4,443,791 | 4/1984 | Risgin et al. | 340/634 |
| 4,785,658 | 11/1988 | Jackson | 73/23 |
| 4,866,400 | 9/1989 | Britton, Jr. et al. | 330/305 |
| 5,317,274 | 5/1994 | Nakagawa et al. | 324/678 |
| 5,410,908 | 5/1995 | Erichsen | 73/31.05 |
| 5,585,756 | 12/1996 | Wang | 327/341 |
| 5,750,880 | 5/1998 | Frers | 73/31.02 |
| 5,793,645 | 8/1998 | Rump et al. | 364/505 |
| 5,808,461 | 9/1998 | Weigold et al. | 324/71.1 |

FOREIGN PATENT DOCUMENTS

| | | |
|---|---|---|
| 546 735 | 6/1993 | European Pat. Off. . |
| 61-104246 | 5/1986 | Japan . |
| 61-104246A | 9/1986 | Japan . |

*Primary Examiner*—Hezron Williams
*Assistant Examiner*—J. David Wiggins
*Attorney, Agent, or Firm*—Kenyon & Kenyon

[57] ABSTRACT

The present invention provides a device for measuring air quality. The device includes at least one sensor with a sensor resistance which is converted via signal processing into an output signal, the gas sensing or air content sensing device having its sensor(s) with electrical resistance that is a function of the air quality, such sensors being connected in an astable flipflop circuit arrangement with a first feedback resistor, a second feedback resistor, a capacitor and a comparator—where the first resistor is coupled between the inverting input and output of the comparator, and the second resistor is coupled between the noninverted input and the output of the comparator, and the sensor(s) is/are coupled between a reference potential and the noninverting input of the comparator. The output signal has a period which is related to the sensor resistance.

5 Claims, 1 Drawing Sheet

AIR QUALITY MEASURING DEVICE

FIELD OF THE INVENTION

The present invention relates to a device for measuring air quality.

BACKGROUND INFORMATION

In the related art, an analog signal controls a voltage-controlled oscillator (VCO). The voltage-controlled oscillator delivers a digital signal whose frequency is a measure of the voltage of the analog signal.

SUMMARY OF THE INVENTION

The present invention provides a trouble-free signal processing system for an air quality sensor.

In one embodiment of the device according to the present invention for measuring air quality, a sensor is provided whose sensor resistance is related to air quality. This sensor resistance is part of a signal processing system that converts the sensor resistance into an output signal with a period which is related to the sensor resistance. The period of the output signal is thus a measure of sensor resistance. This frequency-determined output signal is less sensitive to received interference or conductor-bound interference than would be an analog signal whose amplitude contains the useful information. Interference due to temperature effects can also be reduced. Time- and frequency-dependent output signals can be detected with a higher resolution than analog signals with some microcontrollers. If a binary signal with a variable period is available as the output signal, simple signal processing using digital technology is possible. This reduces the need for expensive analog components.

Voltage-time or voltage-frequency converters may be used for signal processing. These circuits, also known as voltage-controlled oscillators, are available as standard integrated circuits or chips.

In another embodiment according to present invention, an astable flipflop arrangement including an RC element and a comparator is used as the voltage-time converter. According to this embodiment, a capacitor is coupled between a reference potential and an inverting input of the comparator, and a first resistor is coupled to the output of the comparator. A sensor resistance is coupled between the reference potential and a non-inverting input of the comparator, and a second resistor is coupled to the output of the comparator. The output signal is picked off at the output of the comparator. This circuit design yields the result that the period of the output signal is a logarithmic function of the sensor resistance. The period of this logarithmic curve corresponds to the sensor resistance/air quality characteristics of the air quality sensors, which are also logarithmic or exponential. This yields a constant sensitivity over several decades. The need for analog log modules, which would also yield a constant sensitivity, is thus reduced. An output signal with a variable period is less susceptible to interference in comparison with the output signal of an analog log module.

The present invention also provides an air quality measuring device for use in motor vehicles. The ventilation systems are regulated as a function of the air quality.

DETAILED DESCRIPTION

Figure 1:
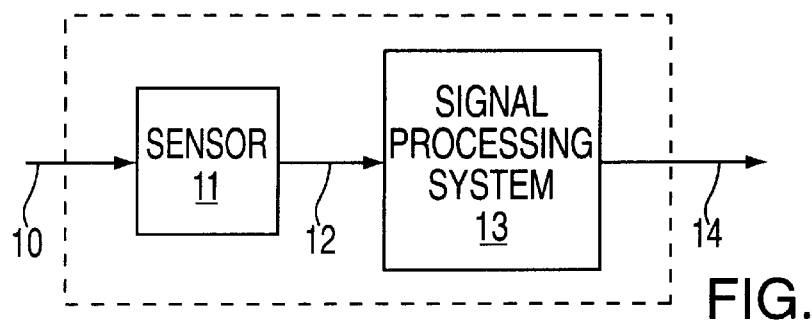
FIG. 1 illustrates a block diagram of a device for measuring air quality.

An air quality 10 is converted by a sensor 11 into a test signal 12. Signal processing system 13 converts this test signal 12 into an output signal 14.

In one embodiment according to the present invention, signal processing system 13 includes a comparator 21, at whose non-inverting input a sensor resistor $R_s$ 17 is connected to a reference potential, and a second resistor R2 19 is connected to the output of comparator 21. A capacitor C 18 is connected to a reference potential at the inverting input of comparator 21, and a resistor R 20 is connected to the output of comparator 21. Output signal 14 is picked off against the reference potential at the output of comparator 21.

Figure 3A:
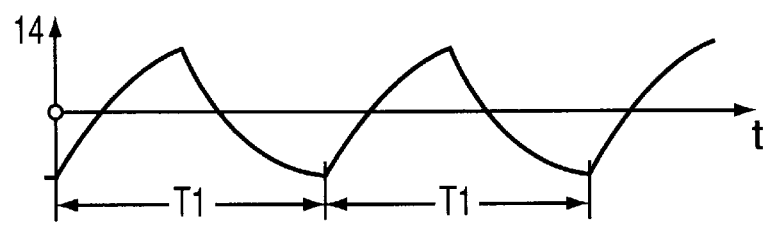
FIG. 3a illustrates an output signal in accordance with an embodiment of the present invention.
Figure 3B:
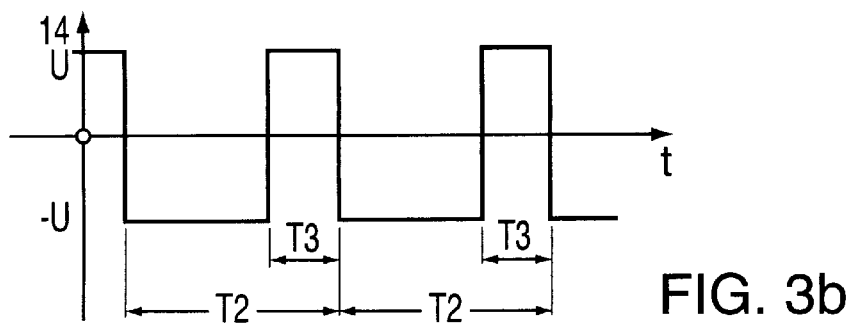
FIG. 3b illustrates the output signal in accordance with another embodiment of the present invention.

FIG. 3a illustrates a graph of the output signal 14 as a function of time. The output signal 14 is characterized by an exponential rise and fall, which is repeated after first period T1. Binary output signal 14 shown in FIG. 3b is repeated with a second period T2. Within this second period T2, binary output signal 14 has a value of logical 1 corresponding to voltage U during a third period T3.

The device for measuring air quality functions as follows: sensor 11 is to determine air quality 10. Air quality 10 is understood in particular to refer to the composition of the air such as the prevailing concentration of carbon monoxide or nitrogen oxide. Sensor resistance $R_s$ 17 of sensor 11 changes as a function of the pollution concentration. The CO and NO sensors conventionally used have an exponential resistance/concentration characteristic. A resistive sensor may also be used as sensor 11. All these sensors 11 deliver as test signal 12 a sensor resistance $R_s$ 17 as a function of air quality 10. Since the characteristics have a correspondingly large value range over several decades because of their exponential function, logarithmic analysis is appropriate to obtain a constant sensitivity.

The ventilation system in a motor vehicle, for example, can be controlled as a function of the air quality. A high pollution concentration, such as that occurring in tunnels, for example, would trigger the fan to shut off and/or ventilation valves to close.

Signal processing system 13 converts test signal 12 into an output signal 14 with variable periods T, T1, T2, T3. Voltage-time or voltage-frequency converters, for example, can be used as signal processing system 13. For example, a voltage proportional to sensor resistance $R_s$ 17 of sensor 11 that is picked off at sensor resistor $R_s$ 17 of sensor 11 serves as the input voltage of these converters. The end effect is to achieve an analog-digital conversion.

With a pulse width converter, the voltage to be measured is compared with a sawtooth voltage. A dual slope analog-digital converter is also suitable for representing an analog voltage as a function of time. The voltage-frequency converter receives as an input quantity, the voltage to be converted, and delivers a train of square-wave pulses. The frequency of these pulses is proportional to the applied voltage. Voltage-frequency conversion can also performed according to the charge balance method. The voltage-frequency characteristic with this known method is a straight line.

Figure 2:
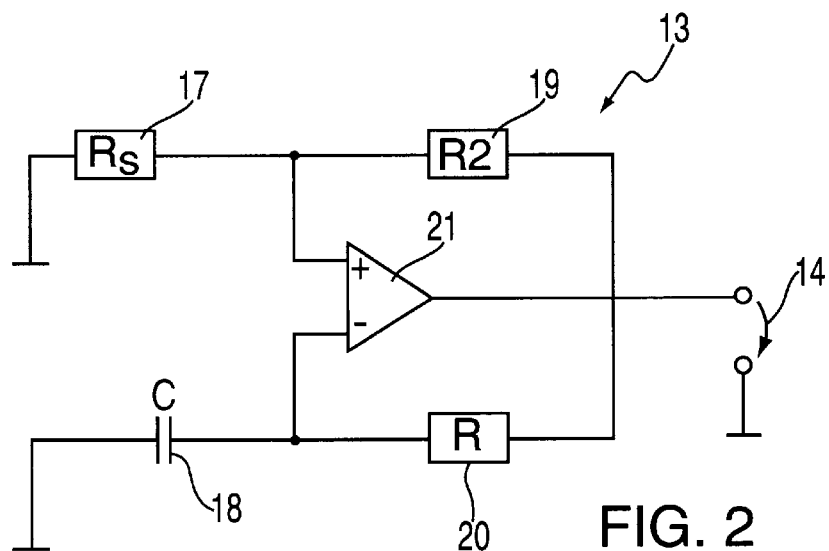
FIG. 2 illustrates a circuit arrangement of one embodiment of the device for measuring air quality.

FIG. 2 illustrates an astable flipflop arrangement, also known as a multivibrator or a relaxation oscillator, which includes an RC element and a comparator. Sensor resistance $R_s$ 17 determines the frequency in this circuit. At the time when the flipflop shown in FIG. 2 is energized, the voltage on the capacitor is zero. Comparator 21 supplies as output signal 14 a positive voltage U, as shown in FIG. 3b. This voltage charges capacitor C 18 across resistor R20. The operating point in the form of the falling voltage on sensor resistance $R_s$ 17 is defined by the voltage divider, including sensor resistor $R_s$ 17 and a second resistor R2 19, and by output signal 14. When the voltage on capacitor C 18 reaches this operating point, comparator 21 flips and supplies an output voltage −U. The charging current of capacitor C 18 is now flowing in the opposite direction. Capacitor C 18 discharges until reaching a second operating point at the negative value of the first operating point. Output signal 14 of comparator 21 again changes polarity, with positive voltage U being applied at the output. The process described above is then repeated.

With the help of the exponential charging and discharging curve of capacitor C 18, periods T, T1, T2, T3 can now be determined mathematically.

$$T = 2^* R^* C^* \ln\left(1 + \frac{2^* R_S}{R2}\right). \quad (1)$$

If the quotient $2R_s/R2$ is much greater than 1, equation (1) is simplified as follows:

$$T = 2^* R^* C^* \ln\frac{2^* R_S}{R2}. \quad (2)$$

This logarithmic relationship between period T and sensor resistance $R_s$ 17 is based on a circuit configuration as illustrated in FIG. 2. An output signal 14 as illustrated in FIG. 3b is realistic for this circuit configuration. Second period T2 shown there corresponds to period T in equations (1) and (2). The logarithmic relationship between period T and sensor resistance $R_s$ 17 is thus adapted to the characteristic of sensor 11 described previously. This permits, in particular, a constant sensitivity over several decades.

The present invention is explicitly not limited to the embodiment illustrated in FIG. 2. Thus, output signal curves, other than those illustrated in FIGS. 3a and 3b, are also contemplated by the present invention. Sensor resistance $R_s$ 17 may be converted, for example, to an output signal 14 having a first period T1, which increases exponentially within first period T1 and then drops again. After first period T1, this exponential rise and fall is repeated. In agreement with FIG. 3b, sensor resistance $R_s$ 17 may be converted to a period T, T1, T2, T3, with a third period T3 being varied at a constant second period T2, which represents a basic period. This corresponds to an influence on the pulse duty factor. In addition, there is the possibility of varying both basic period T2 and the pulse duty factor through T3. Suitable modulation methods are to be used for this purpose.

Standard components are available for determining period T, T1, T2, T3 which depends on sensor resistance $R_s$ 17. In addition to digital determination, conversion to an analog voltage is also possible. Some micro-controllers are characterized in that analog voltages are measured with 8-bit resolution, for example, but times are measured with 16-bit resolution.

In the circuit configuration illustrated in FIG. 2, the common reference potential is ground. However, this is not necessarily the case. For example, it is quite feasible to bring sensor resistance $R_s$ 17 and capacitor C 18 to a common reference potential, whereas output signal 14 is picked off against a second reference potential which matches a potential supplied to comparator 21. In this way, signal adjustments can be performed in a controlled manner.

I claim:

1. A air sensing device for measuring air quality, comprising:

at least one sensor having a electrical resistance which is a function of the air quality; and an astable flipflop circuit arrangement including a first feedback resistor, a second feedback resistor, a capacitor and a comparator, the first resistor being coupled between an inverting input of the comparator and an output of the comparator, the second resistor being coupled between a noninverting input of the comparator and the output of the comparator, the capacitor being coupled between a reference voltage and the inverting input of the comparator, the at least one sensor being coupled between a reference potential and the noninverting input of the comparator, and the output of the comparator providing an output signal.

2. The device according to claim 1, wherein a resistance of the second resistor is much smaller than the resistance of the at least one sensor.

3. The device according to claim 1, wherein the resistance of the at least one sensor is a resistive resistance.

4. The device according to claim 1, wherein the output signal has a period that is a logarithmic function of the resistance of the at least one sensor.

5. An air quality measuring device with air sensing capability for controlling a ventilation system in a motor vehicle, comprising:

at least one sensor having a electrical resistance which is a function of the air quality;

an astable flipflop circuit arrangement including a first feedback resistor, a second feedback resistor, a capacitor and a comparator, the first resistor being coupled between an inverting input of the comparator and an output of the comparator, the second resistor being coupled between a noninverting input of the comparator and the output of the comparator, the capacitor being coupled between a reference voltage and the inverting input of the comparator, the at least one sensor being coupled between a reference potential and the noninverting input of the comparator, the output of the comparator providing an output signal; and the ventilation system controlled by a control signal which is a function of the output signal.

* * * * *